US008052980B2

(12) United States Patent
Aoki et al.

(10) Patent No.: US 8,052,980 B2
(45) Date of Patent: *Nov. 8, 2011

(54) USE OF THE NEUROTOXIC COMPONENT OF A BOTULINUM TOXIN FOR TREATING ARTHRITIS

(75) Inventors: K. Roger Aoki, Laguna Hills, CA (US); Michael W. Grayston, Irvine, CA (US); Steven R. Carlson, Laguna Niguel, CA (US); Judith M. Leon, Laguna Niguel, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/550,331

(22) Filed: Aug. 28, 2009

(65) Prior Publication Data

US 2009/0318360 A1 Dec. 24, 2009

Related U.S. Application Data

(63) Continuation of application No. 10/933,723, filed on Sep. 2, 2004, which is a continuation of application No. 08/627,118, filed on Apr. 3, 1996, now Pat. No. 6,974,578, which is a continuation of application No. 08/173,996, filed on Dec. 28, 1993, now abandoned.

(51) Int. Cl.
*A61K 39/08* (2006.01)
(52) U.S. Cl. ............. 424/247.1; 514/21.2; 530/324
(58) Field of Classification Search .............. None
See application file for complete search history.

(56) References Cited

U.S. PATENT DOCUMENTS

| | | | |
|---|---|---|---|
| 4,935,969 A | 6/1990 | Farnsworth | |
| 5,298,019 A | 3/1994 | Borodic | |
| 5,401,243 A | 3/1995 | Borodic | |
| 5,512,547 A | 4/1996 | Johnson et al. | |
| 5,562,907 A | 10/1996 | Arnon | |
| 5,696,077 A * | 12/1997 | Johnson et al. | 424/239.1 |
| 5,714,468 A | 2/1998 | Binder et al. | |
| 5,766,605 A | 6/1998 | Sanders et al. | |
| 6,063,768 A * | 5/2000 | First | 514/14 |
| 6,113,915 A * | 9/2000 | Aoki et al. | 424/236.1 |
| 6,235,289 B1 * | 5/2001 | Aoki et al. | 424/236.1 |
| 6,290,961 B1 | 9/2001 | Aoki et al. | |
| 6,306,403 B1 | 10/2001 | Donovan | |
| 6,319,505 B1 | 11/2001 | Aoki et al. | |
| 6,333,037 B1 * | 12/2001 | Aoki et al. | 424/236.1 |
| 6,372,226 B2 * | 4/2002 | Aoki et al. | 424/236.1 |
| 6,395,277 B1 | 5/2002 | Graham | |
| 6,448,231 B2 | 9/2002 | Graham | |
| 6,458,365 B1 | 10/2002 | Aoki et al. | |
| 6,500,436 B2 | 12/2002 | Donovan | |
| 6,623,742 B2 | 9/2003 | Voet | |
| 6,683,049 B1 | 1/2004 | Aoki et al. | |
| 6,841,156 B2 | 1/2005 | Aoki et al. | |
| 6,872,397 B2 | 3/2005 | Aoki et al. | |
| 6,887,476 B2 * | 5/2005 | Aoki et al. | 424/184.1 |
| 6,896,886 B2 | 5/2005 | Aoki et al. | |
| 6,939,852 B2 | 9/2005 | Graham | |
| 6,974,578 B1 | 12/2005 | Aoki et al. | |
| 7,091,176 B2 * | 8/2006 | Aoki et al. | 514/18.3 |
| 7,381,700 B2 * | 6/2008 | Aoki et al. | 514/18.3 |
| 2001/0018415 A1 | 8/2001 | Aoki et al. | |
| 2002/0102275 A1 | 8/2002 | Graham | |
| 2003/0118598 A1 | 6/2003 | Hunt | |
| 2004/0014663 A1 | 1/2004 | Aoki et al. | |
| 2004/0126396 A1 | 7/2004 | Aoki et al. | |
| 2004/0126397 A1 | 7/2004 | Aoki et al. | |
| 2004/0151740 A1 | 8/2004 | Aoki et al. | |
| 2005/0084504 A1 | 4/2005 | Aoki et al. | |
| 2005/0112146 A1 | 5/2005 | Graham | |

FOREIGN PATENT DOCUMENTS

| | | |
|---|---|---|
| DE | 19852981 | 5/2000 |
| EP | 1477183 B1 | 2/2005 |
| GB | 2272697 | 5/1994 |
| WO | WO 93/05800 | 4/1993 |
| WO | WO 94/00481 | 6/1993 |
| WO | WO 94/00081 | 1/1994 |
| WO | WO 94/28922 | 6/1994 |
| WO | WO 94/15629 | 7/1994 |
| WO | WO 94/28923 | 12/1994 |
| WO | WO 95/17904 | 7/1995 |
| WO | WO 95/30431 | 11/1995 |

OTHER PUBLICATIONS

Tse et al., 'Preperation and Characterisation of Homogenous Neurotoxin Type A From *Clostridium botulinum*' Eur. J. Biochem. vol. 122, No. 3 (1982), pp. 493-500.*
Arthritis. Medline Plus Medical Encyclopedia. Feb. 2010. [Retrieved Jun. 13, 2010]. Retrieved from the Internet <http://www.nlm.nih.gov/medlineplus/ency/article/001243.htm.>.*
"Botulinum-Toxin hilft bei Augenleiden"(Dec. 1986).
"Cervical Dystonia"[www.fpnotebook.com/NEU151.htm]; pp. 1-2, (retrieved Sep. 3, 2003).
Communication from the European Patent Office dated Sep. 27, 2007.

(Continued)

*Primary Examiner* — Anish Gupta
(74) *Attorney, Agent, or Firm* — Hal Gibson; Debra Condino

(57) ABSTRACT

A method for treating a patient suffering from arthritis and associated pain include the administration to the patient of a therapeutically effective amount of a neurotoxic component of neurotoxin selected from a group consisting of Botulinum toxin types A, B, C, D, E, F and G.

9 Claims, No Drawings

OTHER PUBLICATIONS

"Enzyme Linked Immuno Sorbent Assays (ELISAS) to Detect Botulinum Toxins Using High Titer-Rabbit Anti-Sera" Botulinum and Tetanus Neurotoxins, Plenum Press, (1993).

"Hyperesthesia Associated with Hyperextension Injuries of the Neck" Injury, vol. 18, No. 4; p. 234, Abstract only, 1987.

"Porton Refocuses on Pharmaceuticals" Scrip, No. 1871, 10 (vol. 9, No. 1993).

Adenis, J.P. et al., "Traitement des Spasmes Faciaux Par La Toxine Botulique a" J.Fr. Ophtalmal., vol. 13, No. 5; pp. 259-264, (1990).

Ambache, J. Physiol., 108; pp. 127-141, (1949).

Ambache, N., "A Further Survey of the Action of Clostridium Botulinum Toxin Upon Different Types of Autonomic Nerve Fibre" J. Physiol.,113; pp. 1-17, (1951).

Borodic et al., "Botulinum B Toxin as an Alternative to Bot. A Toxin: A Histologic Study,"Oph. Plastic and Recon. Sur., vol. 9(3); pp. 182-190 • 1993.

Clark, J.B., "Cervical Dystonia Following Exposure to High-G Forces" Aviat. Space Environ. Me., vol. 61; pp. 935-937, (1990).

Das, T.K. et al., "Effect of treatment with Botulinum toxin on spasticity" Postgraduate Medical Journal, vol. 65; pp. 208-210, (1989).

Habermann "Foreword" Botulinum and Tetanus Neurotoxins, published by Plenum Press; pp. v-ix, (1993).

Dykstra, D. et al., "Treatment of Detrusor-Sphincter Dyssynergia with Botulinum A Toxin: A Double-Blind Study" Arch. Phys. Med. Rehabil., vol. 71; pp. 24-26, (Jan. 1990).

Foster, K.A., "New Wrinkle on Pain Relief: Re-Engineering Clostridial Neurotoxins for Analgesics" Drug Discovery Today, vol. 10, No. 8; pp. 563-569, (Apr. 2005).

Greene, et al., "Development of Antibodies to Botulinum Toxin Type A in Patients with Torticollis Treated wiht Injections of Botulinum Toxin Type A" Botulinum and Tetanus Neurotoxins, Plenum Press; pp. 651-654, (1993).

Greene, et al., "Use of Botulinum Toin Type F Injection to Treat Torticollis in Patients with Immunity of Botulinum Toxin type A" Movement Disorders, vol. 8, No. 4; pp. 479-483, (1993).

Hambleton, P., "Clostridum Botulinum Toxins: a general review of involvement in disease, structure, mode of action and preparation for clinical use" J. Neurol., vol. 239, No. 1; pp. 16-20, (1992).

Harper, K.E., et al., "Frey's Syndrome" International Journal of Dermatology, vol. 25, No. 8; pp. 524-526, (Oct. 1986).

Hatherway, C.L., "Bacterial Sources of Clostridial Neurotoxins" Botulinum Neurotoxin and Tetanus Toxin Academic Press, pp. 4-24, (1989).

Heneson, "Deadly toxin calms excited muscles,"Science, p. 24 (1990).

Jankovic, et al., "Therapy with Botulinum Toxin" Botulinum and Tetanus Neurotoxins, Plenum Press, (1993).

Jankovic et al., "Therapeutic Uses of Botulinum Toxin" , The New Eng. J. of Med., p. 1186 (Apr. 25, 1991).

Jenzer, G., et al., "Type B Botulism, Report on Mild Courses with Predominantly Autonomic Nervous Impairement"Schweiz. Med. Wschr, vol. 104; pp. 685-693, (1974), with English translation.

Khalafalla, et al., "Botulinum Toxin and Sweating" J. Neurology, Neurosurgery and Psychiatry, 57; pp. 1437-1438, (1994).

Knight, "Botulinum Toxin Types A, B and D Inhibit Catecholamine Secretion from Bovine Adrenal Medullary Cells," FEBS Lett., vol. 207(2); pp. 222-228, 1986.

Kondo et al., "Modification of the Action of Pentagastrin on acid secretion by botulinum toxin" Experientia, vol. 33(6); pp. 750-751, 1977.

Konstazer, A. et al., "Lokale Injektionsbehandlung mit Botulinum-Toxin A bei schwerer Arm-und Beinspastik" Der Nervenarzt, vol. 64(8); pp. 517-523, (Aug. 1993).

Laccourreye, et al., "Treatment of Frey's Syndrome in Topical 2% Diphemanil Methylsulfate (Prantal): A Double-Blind Evaluation of 15 Patients" Laryngoscope, vol. 100; pp. 651-653, (1990).

Ludlow, et al., "Therapeutic Uses of Type F Botulinum Toxin" Letter to New England Journal of Medicine, vol. 326, No. 5; pp. 349-350, (Jan. 1992).

Memin, et al., "Traitement de la Spasticité 212-214, par la Toxine Botulique" Rev. Neurol., vol. 148(3); pp. 212-214, (1992).

Montecucco, C., et al., "Botulinum Neurotoxins: Mechanism of Action and Therapeutic Applications" Mol. Med. Today, vol. 2, No. 10; pp. 418-424, (Oct. 1996).

Moyer, E., et al. "Botulinum Toxin Type B: Experimental and Clinical Experience" Therapy with Botulinum Toxin, Jankovic J. and Hallett, M., ed., Dekker Publishers; New York, NY; pp. 71-85, (Feb. 1994).

Price et al., "A Comparative Study of Tear Secretion in Blepharospasm and Hemifacial Spasm Patients treated with Botulinum Toxin," J. of Clin. Neuro, vol. 13(1); pp. 67-71 (1993).

Ransom, G.M., et al., "Enzyme-Linked Immunosorbent Assays (ELISAs) to Detect Botulinum Toxins Using High Titer Rabbit Anti-Sera" Botulinum and Tetanus Neurotoxins, Plenum Press; pp. 449-462, (1993).

Ruusuvaara, P and Setala, K., "Long-term Treatment of Involuntary Facial Spasms Using Botulinum Toxin" Acta Opthal., vol. 68; pp. 331-338, (1990).

Saga, T., et al., "Secretion of Tears in Patients with Hemifacial Spasm" Jpn. J. Opthalmor., vol. 34; pp. 30-35, (1990).

Schantz et al., "Properties and Use of Botulinum Toxin and Other Microbial Neurotoxins in Medicine" Mirco. Reviews, pp. 80-99 (Mar. 1992).

Schantz et al., "Quality of Botulinum Toxin for Human Treatment,"Bot. and Tetanus Neuro., pp. 41-49 (1993).

Schantz et al., "Preparation and Characterization of Botulinum Toxin Type a for Human Treatment," Therapy with Botulinum Toxin, pp. 657-659 (1994).

Schiavo et al., "Tetanus and Botulism Neurotoxins: Isolation and Assay,"Methods Enzymol., vol. 248; pp. 643-652 (1995).

Schurch, B., et al., "Effets de la Toxine Botulinique A sur le sphincter strié péériurétral des vessies neurogénes" Journal d'Urologie, vol. 96(7); pp. 375-380, (1990).

Scott, Alan B., "A Clinical Preface" Botulinum and Tetanus Neurotoxins, Plenum Press; pp. 557-558, (1993).

Sellin et al., "Different effects of types A and B botulinum toxin on transmitter release at the rat neuromuscular junction," Acta. Physiol. Scan., vol. 119; pp. 127-133 (1983).

Simpson et al., "Botulinum neurotoxin type E: studies on mechanisms of action and on structure-activity relationships"J. Pharmacol Exp Ther., vol. 224; pp. 135-140 (1983).

"Starkes Toxin hilft bei Blapharospasmus"(Oct. 10, 1987).

Tang-Liu, D., et al., "Intramuscular Injection of $^{125}$I-botulinum Neurotoxin-Complex Versus $^{125}$I-botulinum-free Neurotoxin: Time Course of Tissue Distribution" Toxicon, vol. 42; pp. 461-489, (2003).

Tsui, J.K., et al., "A Pilot Study on the Use of Botulinum Toxin in Spasmodic Torticollis", Can. J. Neurol. Sci., vol. 1, No. 4; pp. 314-316, (1985).

Wainwright, R.B. et al., "Food-Borne Botulism in Alaska, 1947-1985: Epidemiology and Clinical Findings" J. Infect. Dis., vol. 157, No. 6; pp. 1158-1162, (1988).

Wohlfarth, et al., "Pharmacokinetic Properties of Different Formulations of Botulinum Neurotoxin Type A" Naunyn Schmiedeberg's Arch. Pharmacol., vol. 365 (Supp 2); R48, (2002).

Zhang et al., "Detection of Botulinum Neurotoxin's Enzymatic Activity of Type A Ghuncha Ambrin," Faseb J., vol. 18(8); 1 page (2004).

Anderson et al., "Botulinum Toxin Treatment of Spasmodic Torticollis," J. of the Royal Soc. Of Med., 1992, 85:524-529.

"Athena files US and Canadian Investigational New Drugs," Scrip, Jun. 5, 1992, No. 1724, p. 29.

"Athena Makes a Wise Move," Med. Advertising News, Nov. 1992, p. 4.

"Athena Outlines Business Strategy," Marketletter, Oct. 5, 1992.

Balkan et al., "A five year analysis of botulinum toxin type A injections: some unusual features," Annals of Ophthalmology, 1991, 23(9):326-333.

Blasi et al., "Botulinum Neurotoxin A Selectively Cleaves the Synaptic Protein SNAP-25," Nature, 1993, 365:160-163.

Berardelli et al., "Botulinum Toxin Treatment in Patients with Focal Dystonia and Hemifacial Spasm. A multicenter study of the Italian Movement Disorder Group," Neurol. Sci, 1993, 14:361-367.

Biglan, "Experience with Botulinum A toxin (Oculinum) in the treatment of strabismus," Contemp. Opth. Forum1987, 5(6): 230-240.

Blitzer et al., "Electromyographic Findings in Focal Laryngeal Dystonia (Spastic Dysphonia)," *Ann. Otol. Rhino. Laryngol.*, 1985, 94:591-594.

Bodde et al., "Transdermal Peptide Delivery," *Biochem. Soc. Trans.*, 1989, 17(5): 943-945.

"Botulinum Toxin for the Treatment of Facial Lines and Wrinkles," 2005, [www.shorelaser.com/BotoxA.html], pp. 1-7.

"Botulinum Toxin may be useful in a range of muscular disorders," *Int. Med. News*, 1991, 15:24(16):36.

Boghen, "Effectiveness of Botulinum Toxin in the Treatment of Spasmodic Torticollis," *Eur. Neurol.*, 1993, 33:199-203.

Borodic et al., "Clinical and scientific aspects of botulinum A toxin," *Ophthalm Clinics of N. America*, 1991, 4(3): 491-503.

Boroff et al., "Amino acid analysis of the isolated and purified components from crystalline toxin of Clostridium botulinum type A," *Infect. Immun.*, 1970, 2(5):679-680.

Brin et al, "Assessment: The clinical usefulness of Botulinum toxin A in treating neurologic disorders," *Neurology*, 1990, 40: 1332-1336.

Brin et al., "Localized Injections of Botulinum Toxin for the Treatment of Focal Dystonia and Hemifacial Spasm," *Advances in Neurology*, 1988, 50:599-608.

Buckelew, "Fibromyalgia: a rehabilitation approach. A review.," *Am. J of Phy. Med. & Rehab.*, 1989, 68(1):37-42.

Callaway, "Botulinum Toxin Type B: Pharmacology and Biochemistry," *Clinics in Dermatology*, 2004, 22:23-29.

Choi et al., "Transdermal delivery of bioactive peptides: the effect of n-decylmethyl sulfoxide, pH, and inhibitors on Enkephalin metabolism and transport," *Pharm. Res.*, 1990, 7(11): 1099-1106.

Cioffi et al., "Microvasculature of the Anterior Optic Nerve," *Surv. Of Ophthal.*, 1994, 38: S107-S116.

Cohen et al., "Treatment of Focal Dystonias of the Hand with Botulinum Toxin Injection" *Neurology*, 1987, 37:123-124.

Cosgrove et al., "Botulinum toxin A prevents the development of contractures in the hereditary spastic mouse model," *Dev. Med. And Child Neurol.*, 1994, 36: 379-385.

Cosgrove et al., "Botulinum toxin in the management of lower limb in cerebral palsy," *Dev. Med. And Child Neurol.*, 1994, 36: 386-396.

Dasgupta et al., "Purification of Clostridium botulinum type A toxin, Biochimica," *Biochim. Biophys. Acta.*, 1970, 214(2):343-349.

Dasgupta et al., "Role of a protease in natural activation of Clostridium botulinum neurotoxin," *Infect. Immun.*, 1972, 6(4):587-590.

Dasgupta et al., "Separation of toxin and Hemagglutinin from crystalline toxin of Clostridium botulinum type A by anion exchange chromatography and determination of their dimensions by gel filtration," *J. Biol. Chem.*, 1969, 243(5):1065-1072.

Dasgupta, "The Structure of Botulinum Neurotoxin," *Botulinum Neurotoxin and Tetanus Toxin*, 1989, pp. 53-67.

Davis et al., "Significant Improvement of Stiff-Person Syndrome After Paraspinal Injection of Botulinum Toxin A," *Movement Disorders*, 1993, 8(3):371-373.

Departments, Programs and Services [www.gillettechildren.org/about-us/staff/departments.html] 2003.

Duane, "Spasmodic Torticollis," *Adv. Neuro.*, 1988, 49: 135-150.

Dunn et al., *Ophthal.*, 1986, 93(4): 470-475.

Eames et al., "The effect of Botulinum toxin A on gastrocnemius length: magnitude and duration of response," *Dev. Med and Child Neurol.*, 1999, 41: 226-232.

"Elan Pharmaceuticals exploring potential use of MYOBLOC (Botulinum Toxin Type B) in Spasticity, Pain and Cermatiolic Applications," [www.biospace.com/news_story.cfm?StoryID=4964504&full=1] 2001.

Elston et al., "Paralytic Strabismus: The Role of Botulinum Toxin," *Br. J. Ophthalmol.*, 1985, 69(12):891-896.

Elston, "Thyroid Eye Disease," *Eye*, 1990, 4(pt. 4):vii.

Elston et al., "Treatment of strabismus in adults with Botulinum toxin A," *Brit. J. of Ophthal.*, 1985, 69(10):718-724.

Escobar et al., "Myofascial Pain Syndrome," *Orth. Review*, 1987, 16(10):708-713.

Eustis et al., "Botulinum Toxin," *Opthal. Clinics of N. Am.*, 1989, 2(1): 163-172.

Gammon et al., "Botulinum chemodenervation treatment of strabismus," *J. Ped. Ophthal. S.*, 1989, 96(7): 931-934.

Gjerstad et al., "Treatment of Focal Dystonia with Botulinum Toxin," *Tidsskrift for Den Norske Laeceforening*, 1991, 111(21):2637-2639.

Goodnough et al., "Stabilization of Botulinum Toxin Type A During Lyophilization," *Applied and Environmental Microbiology*, 1992, 58(10):3426-3428.

Greene et al., "Response to Botulinum Toxin F in Seronegative Botulinum Toxin A-Resistant Patients," *Movement Disorders*, 1996, 11(2):181-184.

Han et al., "Effect of botulinum toxin A chemodenervation in sensory strabismus," *Journal of Pediatric Ophthalmology and Strabismus*, 2001, 38(2):68-71.

Humphry, "Botulinum Toxin: A New Ally of an old adversary," *BMJ*, 1989, 298:136-137.

Jankovic et al., "Botulinum A toxin for cranial-cervical dystonia: A double-blind, placebo-controlled study," *Neurology*, 1987, 37:616-623.

Jedynak et al., "Treatment of spasmodic torticollis by local injections of Botulinum toxin," *Rev. Neurol.*, 1990, 146:440-443.

Jost et al., "Efficacy and tolerability of a botulinum toxin type A free of complexing proteins (NT 201) compared with commercially available botulinum toxin type A (BOTOX(R)) in healthy volunteers," *J. Neurol. Transm.*, 2005, 112: 905-913.

Kohl et al., "Comparison of the effect of Botulinum A BOTOX with highly purified neurotoxin (NT201) in the extensor digitorum brevis muscle test," *Movement Disorders*, 2000, 15:165.

Lewis, "Wrinkles in Motion the Ultimate Guide," 2002 [website].

Liedtke et al., "Transdermal administration of insulin in type II diabetes, Results of a clinical pilot study," *Arneimeittelforschunq*, 1990, 40(8): 884-886.

Magoon, *Ophthal.*, 1989, 96(7): 931-934.

Magoon, "Botulinum Toxin chemo-denervation for strabismus in infants and children," *J. Ped. Ophthal. S.*, 1984, 21(3): 110-113.

Melling et al., *Eye*, 1988, 2:16-23.

Mezaki et al., "Combined use of Type A and F Botulinum Toxins for Blepharospasm: A Double-Blind Control Trial," *Movement Disorders*, 1999, 14(6):1017-1020.

Moyer et al., "Effects of Intramuscular Injection of Botulinum Toxin Type B in Nonhuman Primates; Botulinum and Tetanus Neurotoxins—Neurotransmission and Biomedical Aspects," *Botulinum and Tetanus Neurotoxins-Neurotransmission and Biomedical Aspects* 1993, Bibhuit R. Dasgupta (Ed.), Plenum Press.

News Publication: "Marketing Approvals," *Med. World News*, 1990, 31(5): 2.

News Publication: "Porton launches Dysport in UK," *Scrip*, 1991, 1607: 23.

News Publication: "U.S. Food & Drug Administration approves coulinum for strabismus in patients 12 years of age and above and for blepharospasm," *Bin. Vis. Quart*, 1990, 5(2): 61.

Overmyer, "Botulinum Toxin: Poison with a purpose" *Mod. Med.*, 1991, 59: 112-116.

Park et al., "Binding of Clostridium Botulinum type B toxin to rat brain synaptosome," *Fems. Micro. Lett.*, 1990, 60(3): 243-247.

Pope, "Approval Unwrinkles Elan's Brow," [http://www.ideaadvisor.com/company/article.asp?aid=7368]. Dec. 11, 2000.

Poewe et al., "Experience with Botulinum Toxin in Cervical Dystonia; Therapy with Botulinum Toxin," 1994, pp. 267-278.

Rader, "Biopharmaceutical Products in the U.S. Market," *Biopharma*, 2001, 332:271-274.

Roggenkamper et al., "Efficacy and safety of a new Botulinum Toxin Type A free of complexing proteins in the treatment of blepharospasm," *J. Neurol. Transm.*, 2006, 113: 303-312.

Rosenbaum et al., "Verical rectus muscle transposition and Botulinum Toxin (Oculinum) to medical rectus for abducens palsy," *Arch. Ophthal.*, 1989, 107(6): 820-823.

Sanchez et al., "Propiedades Farmacologicas y Usos Terapeuticos de la Toxina Botulinica," *Farmacia Clinica*, 1992, 9(5):404-413.

Sanders et al, "Drug delivery systems and routs of administration of peptide and protein drugs," *Eur. J. of Drug Met. And Pharma*, 1990, 12(2): 95-102.

Sasaki et al., "Effect of pyrrolidone derivatives on lipid membrane and protein conformation as transdermal penetration enhancer," *J. Pharmacobio-Dyn*, 1990, 13: 468-474.

Sato et al., "Purification and some properties of a proteinase and an esterase released from Clostridium Botulinum A, B, and F types," *Nippon Saik. Zasshi*, 1973, 28(4): 367-374.

Savino et al., "Hemifacial Spasm treated with Botulinum A toxin injection," *Arch. Ophthalmol.*, 1985, 103(9):1305-1306.

Schantz, "Use of crystalline type A botulinum toxin in medical research," *Biomedical aspects of botulism*, 1981, Academic Press, New York, pp. 143-150.

Schiavo et al., "Botulinum Neurotoxins are Zinc Proteins," *J. Bol. Chem.*, 1992, 267(33):23479-23483.

Schwartz, "Circulatory Defects of the Optic Disk and Retina in Ocular Hypertension and High Pressure Open Angle Glaucoma," *Survey of Ophthal.*, 1994, 38.

Scott et al., "Systemic Toxicity of Botulinum Toxin by Intramuscular Injection in the Monkey," *Movement Disorders*, 1988, 3(4):333-335.

Scott, "Botulinum Toxin Treatment of Strabismus and Blepharospasm, a multiple investigator study," *Proceedings of the 5th meeting of the internat'l strabismological association*, 1986, 483-485.

Scott, "vol. VII Module 12: Botulinum Toxin treatment of strabismus," *Am. Aca. Ophthal.*, 1989, 2:1-11.

Scott et al., *Ophthal.*, 1985, 92(5): 676-683.

Scott et al., "Botulinum treatment of strabismus in children," *Trans. Am. Ophthal. Soc.*, 1990, 87: 174-180, 180-184.

Simpson, "Current Concepts of the Mechanism of Action of Clostridial Neurotoxins," *Botulinum and Tetanus Neurotoxins*, 1993, Plenum Press, New York, pp. 1-15.

Simpson, "The Origin Structure and Pharmacological Activity of Botulinum Toxin," *Pharmacol. Reviews*, 1981, 33 3 :155-188.

Simpson, "Clinically Relevant Aspects of the Mechanism of Action of Botulinum Neurotoxin," *Journal of Voice*, 1992, 6(4):358-364.

Simons, "Fibrositis/fibromyalgia: a form of myofascial trigger points?," *Am. J. of Med.*, 1986, 81(3A):93-98.

Snow et al., "Treatment of Spasticity with Botulinum Toxin: A Double-Blind Study" *Annals of Neurology*, 1990, 28(4):512-515.

Southern Utah Spine & Rehabilitation Special Treatment and Tests [http://physical-medicine.net/special.htm] • 2001.

Srinivisan et al., "Iontophoresis of polypeptides: effect of ethanol pretreatment of human skin," *J. Pharma. Sci.*, 1990, 79(7).

Stacy et al., "Efficacy of Botulinum toxin type B for treatment of blepharospasm: Report of two cases," *Naunyn-Schmiedeberg's Archives of Pharmacology*, 2002, 365(2):R44.

Tonneson et al., "A double blind trial of a 16-hour transdermal nicotine patch in smoking cessation," *New Eng. J. Med.*, 1991, 325(5): 311-315.

Truong et al., "BotB (Botulinum Toxin Type B): Evaluation of Safety and Tolerability in Botulinum Toxin Type A-Resistant Cervical Dystonia Patients (Preliminary Study)," *Movement Disorders*, 1997, 12(5):772-775.

Tse et al., "Preparation and characterization of Homogenous Nerutoxin type a from clostridium botulinum," *Eur. J. Biochem.*, 1982, 122:493-500.

Tsui et al., "Botulinum Toxin Type B in the Treatment of Cervical Dystonia: A Pilot Study," *Neurology*, 1995, 45(11):2109-2110.

Tsui et al., "Local Treatment Spasmodic Torticollis with Botulim Toxin," *Le Journal Canadien des Sci. Neuro.*, 1987, 14(3):533-535.

U.S. Food & Drug Administration, "List of Orphan Designations and Approvals," 2000, pp. 1, 42-46.

Verhoef et al., "Transport of peptide and protein drugs across biological membranes," *Eur. J. Drug Metab.*, 1990, 15(2): 83-93.

Wagman et al., "Botulinum Type A toxin: properties of a toxic dissociation product," *Arch. Biochem. Biophys.*, 1953, 45:375-383.

Wright et al., "The Spastic Mouse and the search for an animal model of spasticity in human beings," *Clin. Orth. And Related Res.*, 1990, 253: 12-19.

Yakovleff et al., "Indications and use of botulinic toxin in the treatment of spasticity," *Annales de Re. et de Med. Phy.* 1994, 36(5):359-363.

"The Merck Manual of Diagnosis and Therapy," 1987, pp. 1420-1421, 1449-1551.

National Institutes of Health, "Clinical Use of Botulinum Toxin, Consensus Development Conference Statement," Nov. 12-14, 1990, http://consensus.nih.gov/1990/1990BotulinumToxin083html.htm, pp. 1-18.

\* cited by examiner

USE OF THE NEUROTOXIC COMPONENT OF A BOTULINUM TOXIN FOR TREATING ARTHRITIS

This application is a continuation of U.S. application Ser. No. 10/933,723, filed Sep. 2, 2004, which is a continuation of U.S. application Ser. No. 08/627,118, filed Apr. 3, 1996, now U.S. Pat. No. 6,974,578, which is a continuation of U.S. application Ser. No. 08/173,996, filed Dec. 28, 1993, now abandoned, the entire contents of these prior patent applications are hereby incorporated by reference in their entireties.

FIELD OF THE INVENTION

The present invention provides novel methods for treating various disorders and conditions, with Botulinum toxins. Importantly, the present invention provides methods useful in relieving pain related to muscle activity or contracture and therefore is of advantage in the treatment of, for example, muscle spasm such as Temporomandibular Joint Disease, low back pain, myofascial pain, pain related to spasticity and dystonia, as well as sports injuries, and pain related to contractures in arthritis.

BACKGROUND OF THE INVENTION

Heretofore, Botulinum toxins, in particular Botulinum toxin type A, has been used in the treatment of a number of neuromuscular disorders and conditions involving muscular spasm; for example, strabismus, blepharospasm, spasmodic torticollis (cervical dystonia), oromandibular dystonia and spasmodic dysphonia (laryngeal dystonia). The toxin binds rapidly and strongly to presynaptic cholinergic nerve terminals and inhibits the exocytosis of acetylcholine by decreasing the frequency of acetylcholine release. This results in local paralysis and hence relaxation of the muscle afflicted by spasm.

For one example of treating neuromuscular disorders, see U.S. Pat. No. 5,053,005 to Borodic, which suggests treating curvature of the juvenile spine, i.e., scoliosis, with an acetylcholine release inhibitor, preferably Botulinum toxin A.

For the treatment of strabismus with Botulinum toxin type A, see Elston, J. S., et al., *British Journal of Opthalmology*, 1985, 69, 718-724 and 891-896. For the treatment of blepharospasm with Botulinum toxin type A, see Adenis, J. P., et al., *J. Fr. Opthalmol.*, 1990, 13 (5) at pages 259-264. For treating squint, see Elston, J. S., *Eye*, 1990, 4(4):VII. For treating spasmodic and oromandibular dystonia torticollis, see Jankovic et al., *Neurology*, 1987, 37, 616-623.

Spasmodic dysphonia has been treated with Botulinum toxin type A. See Blitzer et al., *Ann. Otol. Rhino. Laryngol*, 1985, 94, 591-594. Lingual dystonia was treated with Botulinum toxin type A according to Brin et al., *Adv. Neurol.* (1987) 50, 599-608. Finally, Cohen et al., *Neurology* (1987) 37 (Suppl. 1), 123-4, discloses the treatment of writer's cramp with Botulinum toxin type A.

The term Botulinum toxin is a generic term embracing the family of toxins produced by the anaerobic bacterium *Clostridium botulinum* and, to date, seven immunologically distinct neurotoxins have been identified. These have been given the designations A, B, C, D, E, F and G. For further information concerning the properties of the various Botulinum toxins, reference is made to the article by Jankovic and Brin, *The New England Journal of Medicine*, No. 17, 1990, pp. 1186-1194, and to the review by Charles L. Hatheway in Chapter 1 of the book entitled *Botulinum Neurotoxin and Tetanus Toxin*, L. L. Simpson, Ed., published by Academic Press Inc. of San Diego, Calif., 1989, the disclosures in which are incorporated herein by reference.

The neurotoxic component of Botulinum toxin has a molecular weight of about 150 kilodaltons and is thought to comprise a short polypeptide chain of about 50 kD which is considered to be responsible for the toxic properties of the toxin, i.e., by interfering with the exocytosis of acetylcholine, by decreasing the frequency of acetylcholine release, and a larger polypeptide chain of about 100 kD which is believed to be necessary to enable the toxin to bind to the pre-synaptic membrane.

The "short" and "long" chains are linked together by means of a simple disulfide bridge. (It is noted that certain serotypes of Botulinum toxin, e.g., type E, may exist in the form of a single chain un-nicked protein, as opposed to a dichain. The single chain form is less active but may be converted to the corresponding dichain by nicking with a protease, e.g., trypsin. Both the single and the dichain are useful in the method of the present invention.)

In general, four physiologic groups of *C. botulinum* are recognized (I, II, III, IV). The organisms capable of producing a serologically distinct toxin may come from more than one physiological group. For example, Type B and F toxins can be produced by strains from Group I or II. In addition, other strains of clostridial species (*C. baratii*, type F; *C. butyricum*, type E; *C. novyi*, type $C_1$ or D) have been identified which can produce botulinum neurotoxins.

Immunotoxin conjugates of ricin and antibodies, which are characterized as having enhanced cytotoxicity through improving cell surface affinity, are disclosed in European Patent Specification 0 129 434. The inventors note that botulinum toxin may be utilized in place of ricin.

Botulinum toxin is obtained commercially by establishing and growing cultures of *C. botulinum* in a fermenter and then harvesting and purifying the fermented mixture in accordance with known techniques.

Botulinum toxin type A, the toxin type generally utilized in treating neuromuscular conditions, is currently available commercially from several sources; for example, from Porton Products Ltd. UK, under the trade name "DYSPORT," and from Allergan, Inc., Irvine, Calif., under the trade name BOTOX®.

It is one object of the invention to provide novel treatments of neuromuscular disorders and conditions with various Botulinum toxin types. It is another object of the present invention to relieve pain with various Botulinum toxin types.

SUMMARY OF THE INVENTION

The present invention provides a method for relieving pain, associated with muscle contractions, a composition and a method of treating conditions such as cholinergic controlled secretions including excessive sweating, lacrimation and mucus secretions and a method for treating smooth muscle disorders including, but not limited to, spasms in the sphincter of the cardiovascular arteriole, gastrointestinal system, urinary, gall bladder and rectum, which method comprises administering to the patient suffering from said disorder or condition a therapeutically effective amount of Botulinum toxin selected from the group consisting of Botulinum toxin types B, C, D, E, F and G.

Each serotype of Botulinum toxin has been identified as immunologically different proteins through the use of specific antibodies. For example, if the antibody (antitoxin) recognizes, that is, neutralizes the biological activity of, for example, type A it will not recognize types B, C, D, E, F or G.

While all of the Botulinum toxins appear to be zinc endopeptidases, the mechanism of action of different serotypes, for example, A and E within the neuron appear to be different than that of Type B. In addition, the neuronal surface "receptor" for the toxin appears to be different for the serotypes.

In the area of use of the Botulinum toxins in accordance with the present invention with regard to organ systems which involve the release of neurotransmitter, it is expected to introduce the toxins A, B, C, D, E, F, and G directly by local injections.

DETAILED DESCRIPTION

The Botulinum toxins used according to the present invention are Botulinum toxins type A, B, C, D, E, F and G.

The physiologic groups of *Clostridium botulinum* types are listed in Table I.

TABLE I

Physiologic Groups of *Clostridium botulinum*

| Group | Toxin Sero-Type | Biochemistry | Milk Digest | Glucose Fermentation | Lipase | Phages & Plasmids | Phenotypically Related *Clostridium* (nontoxigenic) |
|---|---|---|---|---|---|---|---|
| I | A, B, F | proteolytic saccharolytic | + | + | + | + | *C. sporogenes* |
| II | B, E, F | nonproteolytic saccharolytic psychotrophic | − | + | + | + | |
| III | C, D | nonproteolytic saccharolytic | + | + | + | + | *C. novyi* |
| IV | G | proteolytic nonsaccharolytic | + | − | − | − | *C. subterminale* |

These toxin types may be produced by selection from the appropriate physiologic group of *Clostridium botulinum* organisms. the organisms designated as Group I are usually referred to as proteolytic and produce Botulinum toxins of types A, B and F. The organisms designated as Group II are saccharolytic and produce Botulinum toxins of types B, E and F. The organisms designated as Group III produce only Botulinum toxin types C and D and are distinguished from organisms of Groups I and II by the production of significant amounts of propionic acid. Group IV organisms only produce neurotoxin of type G. The production of any and all of the Botulinum toxin types A, B, C, D, E, F and G are described in Chapter 1 of *Botulinum Neurotoxin and Tetanus Toxin*, cited above, and/or the references cited therein. Botulinum toxins types B, C, D, E, F and G are also available from various species of clostridia.

Currently fourteen species of clostridia are considered pathogenic. Most of the pathogenic strains produce toxins which are responsible for the various pathological signs and symptoms. Organisms which produce Botulinum toxins have been isolated from botulism outbreaks in humans (types A, B, E and F) and animals (types C and D). Their identities were described through the use of specific antitoxins (antibodies) developed against the earlier toxins. Type G toxin was found in soil and has low toxigenicity. However, it has been isolated from autopsy specimens, but thus far there has not been adequate evidence that type G botulism has occurred in humans.

Preferably, the toxin is administered by means of intramuscular injection directly into a local area such as a spastic muscle, preferably in the region of the neuromuscular junction, although alternative types of administration (e.g., subcutaneous injection), which can deliver the toxin directly to the affected region, may be employed where appropriate. The toxin can be presented as a sterile pyrogen-free aqueous solution or dispersion and as a sterile powder for reconstitution into a sterile solution or dispersion.

Where desired, tonicity adjusting agents such as sodium chloride, glycerol and various sugars can be added. Stabilizers such as human serum albumin may also be included. The formulation may be preserved by means of a suitable pharmaceutically acceptable preservative such as a paraben, although preferably it is unpreserved.

It is preferred that the toxin is formulated in unit dosage form; for example, it can be provided as a sterile solution in a vial or as a vial or sachet containing a lyophilized powder for reconstituting a suitable vehicle such as saline for injection.

In one embodiment, the Botulinum toxin is formulated in a solution containing saline and pasteurized human serum albumin, which stabilizes the toxin and minimizes loss through non-specific adsorption. The solution is sterile filtered (0.2 micron filter), filled into individual vials and then vacuum-dried to give a sterile lyophilized powder. In use, the powder can be reconstituted by the addition of sterile unpreserved normal saline (sodium chloride 0.9% for injection).

The dose of toxin administered to the patient will depend upon the severity of the condition; e.g., the number of muscle groups requiring treatment, the age and size of the patient and the potency of the toxin. The potency of the toxin is expressed as a multiple of the $LD_{50}$ value for the mouse, one unit (U) of toxin being defined as being the equivalent amount of toxin that kills 50% of a group of 18 to 20 female Swiss-Webster mice, weighing about 20 grams each.

The dosages used in human therapeutic applications are roughly proportional to the mass of muscle being injected. Typically, the dose administered to the patient may be up from about 0.01 to about 1,000 units; for example, up to about 500 units, and preferably in the range from about 80 to about 460 units per patient per treatment, although smaller of larger doses may be administered in appropriate circumstances such as up to about 50 units for the relief of pain and in controlling cholinergic secretions.

As the physicians become more familiar with the use of this product, the dose may be changed. In the Botulinum toxin type A, available from Porton, DYSPORT, 1 nanogram (ng) contains 40 units. 1 ng of the Botulinum toxin type A, available from Allergan, Inc., i.e., BOTOX®, contains 4 units. The potency of Botulinum toxin and its long duration of action mean that doses will tend to be administered on an infrequent basis. Ultimately, however, both the quantity of toxin administered and the frequency of its administration will be at the discretion of the physician responsible for the treatment and will be commensurate with questions of safety and the effects produced by the toxin.

In some circumstances, particularly in the relief of pain associated with sports injuries, such as, for example, charleyhorse, botulinum type F, having a short duration activity, is preferred.

The invention will now be illustrated by reference to the following nonlimiting examples.

In each of the examples, appropriate areas of each patient are injected with a sterile solution containing the confirmation of Botulinum toxin. Total patient doses range from about 0.01 units to 460 units. Before injecting any muscle group, careful consideration is given to the anatomy of the muscle group, the aim being to inject the area with the highest concentration of neuromuscular junctions, if known. Before injecting the muscle, the position of the needle in the muscle is confirmed by putting the muscle through its range of motion and observing the resultant motion of the needle end. General anesthesia, local anesthesia and sedation are used according to the age of the patient, the number of sites to be injected, and the particular needs of the patient. More than one injection and/or sites of injection may be necessary to achieve the desired result. Also, some injections, depending on the muscle to be injected, may require the use of fine, hollow, teflon-coated needles, guided by electromyography.

Following injection, it is noted that there are no systemic or local side effects and none of the patients are found to develop extensive local hypotonicity. The majority of patients show an improvement in function both subjectively and when measured objectively.

Example 1

The Use of Botulinum Toxin Type in the Treatment of Tardive Dyskinesia

A male patient, age 45, suffering from tardive dyskinesia resulting from the treatment with an antipsychotic drug, such as Thorazine or Haldol, is treated with 150 units of Botulinum toxin type B by direct injection of such toxin into the facial muscles. After 1-3 days, the symptoms of tardive dyskinesia, i.e., orofacial dyskinesia, athetosis, dystonia, chorea, tics and facial grimacing, etc. are markedly reduced.

Example 1(a)

The method of Example 1 is repeated, except that a patient suffering from tardive dyskinesia is injected with 50-200 units of Botulinum toxin type C. A similar result is obtained.

Example 1(b)

The method of Example 1 is repeated, except that a patient suffering from tardive dyskinesia is injected with 50-200 units of Botulinum toxin type D. A similar result is obtained.

Example 1(c)

The method of Example 1 is repeated, except that a patient suffering from tardive dyskinesia is injected with 50-200 units of Botulinum toxin type E. A similar result is obtained.

Example 1(d)

The method of Example 1 is repeated, except that a patient suffering from tardive dyskinesia is injected with 50-200 units of Botulinum toxin type F. A similar result is obtained.

Example 1(e)

The method of Example 1 is repeated, except that a patient suffering from tardive dyskinesia is injected with 50-200 units of Botulinum toxin type G. A similar result is obtained.

Example 2

The Use of Botulinum Toxin Type B in the Treatment of Spasmodic Torticollis A male, age 45, suffering from spasmodic torticollis, as manifested by spasmodic or tonic contractions of the neck musculature, producing stereotyped abnormal deviations of the head, the chin being rotated to one side, and the shoulder being elevated toward the side at which the head is rotated, is treated by injection with 100-1,000 units of Botulinum toxin type E. After 3-7 days, the symptoms are substantially alleviated; i.e., the patient is able to hold his head and shoulder in a normal position.

Example 2(a)

The method of Example 2 is repeated, except that a patient suffering from spasmodic torticollis is injected with 100-1,000 units of Botulinum toxin type B. A similar result is obtained.

Example 2(b)

The method of Example 2 is repeated, except that a patient suffering from spasmodic torticollis is injected with 100-1,000 units of Botulinum toxin type C. A similar result is obtained.

Example 2(c)

The method of Example 2 is repeated, except that a patient suffering from spasmodic torticollis is injected with 100-1,000 units of Botulinum toxin type D. A similar result is obtained.

Example 2(d)

The method of Example 2 is repeated, except that a patient suffering from spasmodic torticollis is injected with 100-1,000 units of Botulinum toxin type E. A similar result is obtained.

Example 2(e)

The method of Example 2 is repeated, except that a patient suffering from spasmodic torticollis is injected with 100-1,000 units of Botulinum toxin type F. A similar result is obtained.

Example 2(f)

The method of Example 2 is repeated, except that a patient suffering from spasmodic torticollis is injected with 100-1,000 units of Botulinum toxin type G. A similar result is obtained.

Example 3

The Use of Botulinum Toxin in the Treatment of Essential Tremor

A male, age 45, suffering from essential tremor, which is manifested as a rhythmical oscillation of head or hand muscles and is provoked by maintenance of posture or movement, is treated by injection with 50-1,000 units of Botulinum toxin type B. After two to eight weeks, the symptoms are substantially alleviated; i.e., the patient's head or hand ceases to oscillate.

Example 3(a)

The method of Example 3 is repeated, except that a patient suffering from essential tremor is injected with 100-1,000 units of Botulinum toxin type C. A similar result is obtained.

Example 3(b)

The method of Example 3 is repeated, except that a patient suffering from essential tremor is injected with 100-1,000 units of Botulinum toxin type D. A similar result is obtained.

Example 3(c)

The method of Example 3 is repeated, except that a patient suffering from essential tremor is injected with 100-1,000 units of Botulinum toxin type E. A similar result is obtained.

Example 3(d)

The method of Example 3 is repeated, except that a patient suffering from essential tremor is injected with 100-1,000 units of Botulinum toxin type F. A similar result is obtained.

Example 3(e)

The method of Example 3 is repeated, except that a patient suffering from essential tremor is injected with 100-1,000 units of Botulinum toxin type G. A similar result is obtained.

Example 4

The Use of Botulinum Toxin in the Treatment of Spasmodic Dysphonia

A male, age 45, unable to speak clearly, due to spasm of the vocal chords, is treated by injection of the vocal chords with Botulinum toxin type B, having an activity of 80-500 units. After 3-7 days, the patient is able to speak clearly.

Example 4(a)

The method of Example 4 is repeated, except that a patient suffering from spasmodic dysphonia is injected with 80-500 units of Botulinum toxin type C. A similar result is obtained.

Example 4(b)

The method of Example 4 is repeated, except that a patient suffering from spasmodic dysphonia is injected with 80-500 units of Botulinum toxin type D. A similar result is obtained.

Example 4(c)

The method of Example 4 is repeated, except that a patient suffering from spasmodic dysphonia is injected with 80-500 units of Botulinum toxin type E. A similar result is obtained.

Example 4(d)

The method of Example 4 is repeated, except that a patient suffering from spasmodic dysphonia is injected with 80-500 units of Botulinum toxin type F. A similar result is obtained.

Example 4(e)

The method of Example 4 is repeated, except that a patient suffering from spasmodic dysphonia is injected with 8-500 units of Botulinum toxin type G. A similar result is obtained.

Example 5

The Use of Botulinum Toxin Types A-G in the Treatment of Excessive Sweating, Lacrimation or Mucus Secretion or Other Cholinergic Controlled Secretions A male, age 65, with excessive unilateral sweating is treated by administering 0.01 to 50 units, of Botulinum toxin, depending upon degree of desired effect. The larger the dose, usually the greater spread and duration of effect. Small doses are used initially. Any serotype toxin alone or in combination could be used in this indication. The administration is to the gland nerve plexus, ganglion, spinal cord or central nervous system to be determined by the physician's knowledge of the anatomy and physiology of the target glands and secretary cells. In addition, the appropriate spinal cord level or brain area can be injected with the toxin (although this would cause many effects, including general weakness). Thus, the gland (if accessible) or the nerve plexus or ganglion are the targets of choice. Excessive sweating, tearing (lacrimation), mucus secretion or gastrointestinal secretions are positively influenced by the cholinergic nervous system. Sweating and tearing are under greater cholinergic control than mucus or gastric secretion and would respond better to toxin treatment. However, mucus and gastric secretions could be modulated through the cholinergic system. All symptoms would be reduced or eliminated with toxin therapy in about 1-7 days. Duration would be weeks to several months.

Example 6

The Use of Botulinum Toxin Types A-G in the Treatment of Muscle Spasms in Smooth Muscle Disorders Such as Sphincters of the Cardiovascular Arteriole, Gastrointestinal System, Urinary or Gall Bladder, Rectal, Etc.

A male, age 30-40, with a constricted pyloric valve which prevents his stomach from emptying, is treated by administering 1-50 units of Botulinum toxin. The administration is to the pyloric valve (which controls release of stomach contents into the intestine) divided into 2 to 4 quadrants, injections made with any endoscopic device or during surgery. In about 1-7 days, normal emptying of the stomach, elimination or drastic reduction in regurgitation occurs.

Example 7

The Use of Botulinum Toxin Types A-G in the Treatment of Muscle Spasms and Control of Pain Associated with Muscle Spasms in Temporal Mandibular Joint Disorders A female, age 35, is treated by administration of 0.1 to 50 units total of Botulinum toxin. The administration is to the muscles controlling the closure of the jaw. Overactive muscles may be identified with EMG (electromyography) guidance. Relief of pain associated with muscle spasms, possible reduction in jaw clenching occurs in about 1-3 days.

Example 8

The Use of Botulinum Toxin Types A-G in the Treatment of Muscle Spasms and Control of Pain Associated with Muscle Spasms in Conditions Secondary to Sports Injuries (Charleyhorse)

A male, age 20, with severe cramping in thigh after sports injury is treated by administration of a short duration toxin, possible low dose (0.1-25 units) of preferably type F to the muscle and neighboring muscles which are in contraction ("cramped"). Relief of pain occurs in 1-7 days.

Example 9

The Use of Botulinum toxin Types A-G in the Treatment of Muscle Spasms and Control of Pain Associated with Muscle Spasms in Smooth Muscle Disorders Such as Gastrointestinal Muscles A female, age 35, with spastic colitis, is treated with 1-100 units of Botulinum toxin divided into several areas, enema (1-5 units) delivered in the standard enema volume, titrate dose, starting with the lowest dose. Injection is to the rectum or lower colon or a low dose enema may be employed. Cramps and pain associated with spastic colon are relieved in 1-10 days.

Example 9

The Use of Botulinum Toxin Types A-G in the Treatment of Muscle Spasms and Control of Pain Associated with Muscle Spasms in Spasticity Conditions Secondary to Stroke, Traumatic Brain or Spinal Cord Injury A male, age 70, post-stroke or cerebral vascular event, is injected with 50 to 300 units of Botulinum toxin in the major muscles involved in severe closing of hand and curling of wrist and forearm or the muscles involved in the closing of the legs such that the patient and attendant have difficulty with hygiene. Relief of these symptoms occurs in 7 to 21 days.

Example 10

The Use of Botulinum Toxin Types A-G in the Treatment of Patients with Swallowing Disorders A patient with a swallowing disorder caused by excessive throat muscle spasms is injected with about 1 to about 300 units of Botulinum toxin in the throat muscles. Relief the swallowing disorder occurs in about 7 to about 21 days.

Example 11

The Use of Botulinum Toxin Types A-G in the Treatment of Patients with Tension Headache A patient with a tension headache caused by excessive throat muscle spasms is injected with about 1 to about 300 units of Botulinum toxin in muscles of the head and upper neck. Relief the tension headache occurs in about 1 to about 7 days.

Although there has been hereinabove described a use of Botulinum toxins for treating various disorders, conditions and pain, in accordance with the present invention, for the purpose of illustrating the manner in which the invention may be used to advantage, it should be appreciated that the invention is not limited thereto since many obvious modifications can be made, and it is intended to include within this invention any such modifications as will fall within the scope of the appended claims. Accordingly, any and all modifications, variations, or equivalent arrangements which may occur to those skilled in the art, should be considered to be within the scope of the present invention as defined in the appended claims.

What is claimed is:

1. A method for treating arthritis pain utilizing a neurotoxic component of a botulinum toxin, the method comprising the step of administering to a patient in need thereof a therapeutically effective amount of the neurotoxic component of the botulinum toxin substantially free of a botulinum toxin complex protein, to thereby treat arthritis pain.

2. The method of claim 1, wherein the botulinum toxin is selected from the group consisting of botulinum toxin types A, B, C, D, E, F and G.

3. The method of claim 1, wherein the neurotoxic component of the botulinum toxin is of a molecular weight of about 150 kilodaltons.

4. The method of claim 1, wherein the botulinum toxin is botulinum toxin type A.

5. The method of claim 1, wherein the botulinum toxin is administered in an amount of between about 0.01 units and about 1000 units.

6. The method of claim 1, wherein the botulinum toxin is administered in an amount of between about 0.01 units and about 500 units.

7. A method for treating arthritis pain utilizing a neurotoxic component of a botulinum toxin, the method comprising the step of administering to a patient in need thereof a therapeutically effective amount of the neurotoxic component of a botulinum toxin type A substantially free of a botulinum toxin complex protein, to thereby treat arthritis pain.

8. The method of claim 7, wherein the botulinum toxin is administered in an amount of between about 0.01 units and about 1000 units.

9. The method of claim 7, wherein the botulinum toxin is administered in an amount of between about 0.01 units and about 500 units.

* * * * *

UNITED STATES PATENT AND TRADEMARK OFFICE
CERTIFICATE OF CORRECTION

| | |
|---|---|
| PATENT NO. | : 8,052,980 B2 |
| APPLICATION NO. | : 12/550331 |
| DATED | : November 8, 2011 |
| INVENTOR(S) | : K. Roger Aoki et al. |

It is certified that error appears in the above-identified patent and that said Letters Patent is hereby corrected as shown below:

On the Title page, in Item (56), under "Other Publications", in column 2, line 1, delete "Preperation" and insert -- Preparation --, therefor.

On Title page 2, in column 1, under "Other Publications", line 9, delete "Ophtalmal.," and insert -- Ophthalmol., --, therefor.

On Title page 2, in column 1, under "Other Publications", line 30, delete "wiht" and insert -- with --, therefor.

On Title page 2, in column 1, under "Other Publications", line 33, delete "Toin" and insert -- Toxin --, therefor.

On Title page 2, in column 1, under "Other Publications", line 36, delete "Clostridum" and insert -- Clostridium --, therefor.

On Title page 2, in column 1, under "Other Publications", line 51, delete "Impairement" and insert -- Impairment --, therefor.

On Title page 2, in column 2, under "Other Publications", line 18, delete "Opthalmor.," and insert -- Ophthalmol., --, therefor.

On Title page 2, in column 2, under "Other Publications", line 20, delete "Mirco." and insert -- Micro. --, therefor.

On Title page 2, in column 2, under "Other Publications", line 25, delete "Type a" and insert -- Type A --, therefor.

On Title page 2, in column 2, under "Other Publications", line 40, delete "Blapharospasmus" and insert -- Blepharospasmus --, therefor.

Signed and Sealed this
Fourteenth Day of February, 2012

David J. Kappos
*Director of the United States Patent and Trademark Office*

CERTIFICATE OF CORRECTION (continued)
U.S. Pat. No. 8,052,980 B2

On Title page 3, in column 1, under "Other Publications", line 60, delete "Cermatiolic" and insert -- Dermatologic --, therefor.

On Title page 3, in column 2, under "Other Publications", line 2, delete "Laeceforening," and insert -- Laegeforening, --, therefor.

On Title page 4, in column 2, under "Other Publications", line 14, delete "Nerutoxin" and insert -- Neurotoxin --, therefor.

On Title page 4, in column 2, under "Other Publications", line 18, delete "Botulim" and insert -- Botulinum --, therefor.

In column 1, line 43, delete "Opthalmology," and insert -- Ophthalmology, --, therefor.

In column 1, line 46, delete "Opthalmol.," and insert -- Ophthalmol., --, therefor.

In column 1, line 65, delete "Hatheway" and insert -- Hathaway --, therefor.

In column 3, in Table I, line 8, delete "psychotrophic" and insert -- psychotropic --, therefor.

In column 3, line 35, delete "the" and insert -- The --, therefor.